United States Patent
Lu et al.

(10) Patent No.: US 11,542,502 B2
(45) Date of Patent: Jan. 3, 2023

(54) APPLICATION OF MICRORNA-210 INHIBITOR IN PREPARATION OF DRUGS FOR TREATING INFLAMMATORY SKIN DISEASES

(71) Applicant: THE SECOND XIANGYA HOSPITAL OF CENTRAL SOUTH UNIVERSITY, Changsha (CN)

(72) Inventors: Qianjin Lu, Changsha (CN); Ming Zhao, Changsha (CN); Yuwen Su, Changsha (CN); Ruifang Wu, Changsha (CN)

(73) Assignee: THE SECOND XIANGYA HOSPITAL OF CENTRAL SOUTH UNIVERSITY, Changsha (CN)

( * ) Notice: Subject to any disclaimer, the term of this patent is extended or adjusted under 35 U.S.C. 154(b) by 0 days.

(21) Appl. No.: 16/978,778

(22) PCT Filed: Jan. 24, 2019

(86) PCT No.: PCT/CN2019/073010
§ 371 (c)(1),
(2) Date: Sep. 8, 2020

(87) PCT Pub. No.: WO2019/174413
PCT Pub. Date: Sep. 19, 2019

(65) Prior Publication Data
US 2021/0284999 A1      Sep. 16, 2021

(30) Foreign Application Priority Data

Mar. 13, 2018 (CN) .......................... 201810205512.X (51) Int. Cl.
*C12N 15/113* (2010.01)
(52) U.S. Cl.
CPC ...... *C12N 15/113* (2013.01); *C12N 2310/141* (2013.01); *C12N 2310/32* (2013.01); *C12N 2310/3515* (2013.01); *C12N 2320/34* (2013.01)
(58) Field of Classification Search
None
See application file for complete search history.

(56) References Cited

U.S. PATENT DOCUMENTS

2011/0172293 A1    7/2011   Fish et al.

FOREIGN PATENT DOCUMENTS

| CN | 105617398 A | 6/2016 | |
| CN | 108144061 A | 6/2018 | |
| WO | 2005013901 A2 | 2/2005 | |
| WO | 2017027839 A1 | 2/2017 | |
| WO | WO-2018065390 A1 * | 4/2018 | ........... C12Q 1/6876 |

OTHER PUBLICATIONS

Ruifang Wu et al., MicroRNA-210 overexpression promotes psoriasis-like inflammation by inducing Th1 and Th17 cell differentiation, The Journal of Clinical Investigation, Jun. 2018, pp. 2551-2568, vol. 128, No. 6.
Zhao Ming et al., miR-210 induces Th17 differentiation in psoriasis vulgaris through targeting STAT6, Journal of Dermatology, 2014, pp. 11, vol. 41.
Erin G. Harper et al., Th17 Cytokines Stimulate CCL20 Expression in Keratinocytes In Vitro and In Vivo: Implications for Psoriasis Pathogenesis, The Society for Investigative Dermatology, 2009, pp. 2175-2183, vol. 129.
Ming Zhao et al., Up-regulation of microRNA-210 induces immune dysfunction via targeting FOXP3 in CD4+ T cells of psoriasis vulgaris, Clinical Immunology, 2014, pp. 22-30, vol. 150.
Soken Tsuchiya et al., MicroRNA-210 Regulates Cancer Cell Proliferation through Targeting Fibroblast Growth Factor Receptor-Like 1 (FGFRL1), Journal of Biological Chemistry, 2010, pp. 1-12.
Guangzhou RiboBio Co., Ltd. "micrOFF mmu-miR-210-3p antagomir, in vivo, 5nmol",(https://www.ribobio.com/en/product_detail/?sku=miR30000658-4-5), date unknown, (accessed Aug. 1, 2022).

* cited by examiner

*Primary Examiner* — Brian Whiteman
(74) *Attorney, Agent, or Firm* — Bayramoglu Law Offices LLC (57) ABSTRACT

Disclosed are methods of using a microRNA-210 inhibitor in preparation of drugs for treating inflammatory skin diseases. The present inventor has demonstrated through a large number of experiments that in vitro inhibition of microRNA-210 expression can significantly enhance the expression of its target gene STAT6, thereby inhibiting proliferation and chemokine CCL20 secretion of keratinocytes, further inhibiting chemotactic T cell migration towards skin lesion, and also inhibiting differentiation of $T_H1$ and $T_H17$. MicroRNA-210 knockout and intradermal injection of a microRNA-210 inhibitor (cholesterol-modified antagomiR-210) on a skin lesion specifically inhibit the expression of microRNA-210, so that skin inflammation in mice can be significantly inhibited, and T cell immune imbalance is mitigated. The present invention provides a new pathophysiological mechanism for inflammatory skin diseases and provides a new strategy for preparing drugs for treating inflammatory skin diseases.

7 Claims, 11 Drawing Sheets

Specification includes a Sequence Listing.

SEQUENCE LISTING

```
<160> NUMBER OF SEQ ID NOS: 4

<210> SEQ ID NO 1
<211> LENGTH: 22
<212> TYPE: RNA
<213> ORGANISM: Homo sapiens

<400> SEQUENCE: 1
agucggcgac agugugcgug uc                                               22

<210> SEQ ID NO 2
<211> LENGTH: 24
<212> TYPE: RNA
<213> ORGANISM: Artificial Sequence
<220> FEATURE:
<223> OTHER INFORMATION: microRNA-210 inhibitor

<400> SEQUENCE: 2
ucagccgcug ugucacacgc acag                                             24

<210> SEQ ID NO 3
<211> LENGTH: 23
<212> TYPE: DNA
<213> ORGANISM: Homo sapiens

<400> SEQUENCE: 3
cacacgcacg cacacgcgcg acg                                              23

<210> SEQ ID NO 4
<211> LENGTH: 22
<212> TYPE: RNA
<213> ORGANISM: Homo sapiens

<400> SEQUENCE: 4
cugugcgugu gacagcggcu ga                                               22
```

APPLICATION OF MICRORNA-210 INHIBITOR IN PREPARATION OF DRUGS FOR TREATING INFLAMMATORY SKIN DISEASES

CROSS REFERENCE TO THE RELATED APPLICATIONS

This application is the national stage entry of International Application No. PCT/CN2019/073010, filed on Jan. 24, 2019, which is based upon and claims priority to Chinese Patent Application No 201810205512.X, filed on Mar. 13, 2018, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBCSRZ005-Sequence Listing-20200826 txt, dated Aug. 26, 2020 and is 759 bytes in size.

TECHNICAL FIELD

The present invention relates to a new medical application of an endogenous non-coding small RNAs inhibitor, more particularly to application of a microRNA-210 inhibitor in preparation of drugs for treating inflammatory skin diseases, and belongs to the field of biomedicine.

BACKGROUND

Inflammatory skin diseases are a kind of common skin diseases jointly mediated by immunocytes and keratinocytes. Abnormal response of the innate immune system, abnormal activation of T lymphocytes, and various inflammatory cytokines and their target cells (keratinocytes) play an important role in the pathogenesis of the inflammatory skin diseases. A series of inflammatory reactions caused by helper T cell ($T_h$ cell) immune imbalance are common in the inflammatory skin diseases. $T_h$ cells are stimulated by some antigen presenting cells and innate immunocytes, and the immune balance among cell subsets is disturbed, so that secretion abnormality of inflammatory cytokines such as interleukins, interferons and tumor necrosis factors is caused. These inflammatory cytokines further act on keratinocytes to induce damage to a skin barrier. For many inflammatory skin diseases, regardless of their complicated causes, most of the pathogenesis of the diseases involves inflammation and immunity, so that immunosuppression or immunoregulation is a main measure for these diseases. However, almost all immunosuppressants have obvious and severe side effects. In recent years, biotherapy has achieved rapid development, and there are more and more monoclonal antibodies, immunoglobulins and biological preparations specific for immune molecules. Although the curative effect is affirmative, the cost is high, adverse reactions cannot be ignored, and long-term use safety is not clear. Therefore, it is of great significance to research and develop novel immunosuppressive or immunoregulation drugs with high curative effect, small side effects and low cost.

MicroRNAs (miRNAs) are a kind of small endogenous non-coding single-stranded RNA molecules, which are in length of about 21 to 25 nucleotides, evolutionarily have highly conserved performance, time sequence and tissue specificity, and are found in almost all multicellular organisms. These small miRNAs generally target one or more mRNAs, regulate gene expression through translational level inhibition or target mRNA breaking, and participate in many physiological and pathological processes in the body. At present, studies have shown that a plurality of miRNAs molecules have significantly different expression in the skin from that in other organs, such as miR-203, miR-146a and miR-31. These miRNAs molecules are either related to functions of keratinocytes or specifically expressed in immunocytes. However, whether these miRNAs molecules can be applied in the preparation of drugs for treating the inflammatory skin diseases is not clear. The present invention firstly proves that expression of microRNA-210 is up-regulated in an imiquimod (IMQ)-induced inflammatory skin lesion, the microRNA-210 regulates proliferation and chemokine secretion of keratinocytes, and regulates the differentiation of Th1 and Th17 cells. Then, the present invention further discloses that an inhibitor targeting microRNA-210 can obviously ameliorate the occurrence and severity of IMQ-induced skin inflammation through in vitro cell experiments and in vivo animal experiments. Our results indicate that the microRNA-210 inhibitor can be applied in the preparation of drugs for treating the inflammatory skin diseases, and has great application prospects in treating patients with the inflammatory skin diseases for skin lesion.

SUMMARY

A first objective of the present invention is to provide application of a microRNA-210 inhibitor in preparation of drugs for treating inflammatory skin diseases. The application provides a new approach for treating the inflammatory skin diseases, and improves treatment effects.

According to the application of the microRNA-210 inhibitor in preparation of drugs for treating inflammatory skin diseases, a sequence of microRNA-210 is as shown by SEQ ID NO: 1.

The inflammatory skin diseases include psoriasis, atopic dermatitis, eczema or parapsoriasis.

The microRNA-210 inhibitor is selected from small interfering RNA, dsRNA, shRNA, microRNA and antisense nucleotide capable of reducing microRNA-210 expression; or a construct capable of expressing or forming the small interfering RNA, dsRNA, shRNA, microRNA and antisense nucleotide.

The microRNA-210 inhibitor is preferably purchased from Guangzhou RiboBio Co, Ltd. A product name is micrOFF™ mmu-miR-210-3p antagomir.

The microRNA-210 inhibitor has a nucleotide sequence of 5'-ucagccgcugugucacacgcacag-3'(SEQ ID NO: 2), and is modified by 3'-cholesterol and 5'-OMe. The modified microRNA-210 inhibitor retains activity of the microRNA-210 inhibitor.

An application method of the microRNA-210 inhibitor is local administration for skin lesion.

A second objective of the present invention is to provide application of a microRNA-210 inhibitor in preparation of a preparation for inhibiting secretion of IL-17A, IL-17F and IFN-γ and promoting secretion of IL-4. A sequence of microRNA-210 is as shown by SEQ ID NO: 1.

A third objective of the present invention is to provide application of a microRNA-210 inhibitor in preparation of a preparation for enhancing expression of a target gene STAT6. A sequence of microRNA-210 is as shown by SEQ ID NO: 1.

A fourth objective of the present invention is to provide application of a microRNA-210 inhibitor in preparation of a preparation for inhibiting proliferation and chemokine CCL20 secretion of keratinocytes and further inhibiting chemotactic T cell migration towards skin lesion. A sequence of microRNA-210 is as shown by SEQ ID NO. 1.

A fifth objective of the present invention is to provide application of a microRNA-210 inhibitor in preparation of a preparation for inhibiting differentiation of $T_H1$ and $T_H17$ and prompting cell differentiation of $T_H2$. A sequence of microRNA-210 is as shown by SEQ ID NO: 1.

The present inventor has demonstrated through a large number of experiments that in an IMQ-induced mouse inflammatory skin lesion, microRNA-210 expression is significantly up-regulated, and in vitro inhibition of microRNA-210 expression can significantly enhance the expression of a target gene STAT6 of microRNA-210, thereby inhibiting proliferation and chemokine CCL20 secretion of keratinocytes, further inhibiting chemotactic T cell migration towards skin lesion, also inhibiting differentiation of $T_H1$ and $T_H17$, and promoting cell differentiation of $T_H2$. Through overexpression of microRNA-210 in the IMQ-induced mouse inflammatory skin lesion (intradermal injection of a microRNA-210 mimic of agomiR-210), skin inflammatory reaction in mice can be obviously promoted and aggravated, and cellular infiltration of $T_H1$ and $T_H17$ in the skin lesion is promoted. Through microRNA-210 knockout and intradermal injection of a microRNA-210 inhibitor (cholesterol-modified antagomiR-210) on the skin lesion, expression of microRNA-210 can be specifically inhibited, skin inflammation in mice can be significantly inhibited, and T cell immune imbalance is mitigated.

BRIEF DESCRIPTION OF THE DRAWINGS

To describe the technical solutions of the present invention more clearly, a brief description of the drawings required for describing the present invention is given below.

FIGS. 3D-3E show influence of microRNA-210 overexpression or inhibition in keratinocytes on T cell chemotaxis.

FIGS. 6A-6D show microRNA-210 regulation on expression of a downstream target gene STAT6

FIGS. 7A-7F show that an IMQ-induced mouse inflammatory skin lesion can be significantly promoted and aggravated through overexpression of microRNA-210 in the skin lesion.

FIGS. 8A-8E shows that an IMQ-induced mouse inflammatory skin lesion can be significantly alleviated through specific microRNA-210 knockout.

FIGS. 9A-9E show that an IMQ-induced mouse inflammatory skin lesion can be significantly mitigated through intradermal injection of antagomiR-210 on a skin lesion.

DETAILED DESCRIPTION OF THE EMBODIMENTS

To make the objectives, technical solutions, and advantages of the present invention clearer, the following further describes the implementations of the present invention in detail with reference to the accompanying drawings. It is to be understood that, these embodiments are merely used for illustrative purposes, and do not limit the protection scope of the present invention.

Figure 1A:
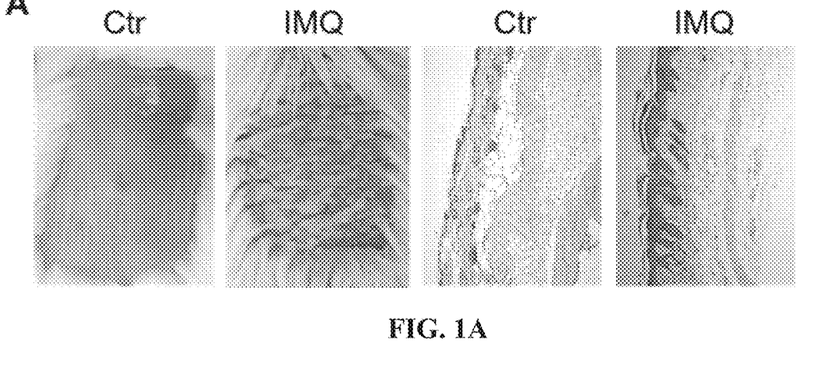
FIG. 1A shows appearances and HE staining pathological sections (amplification factor: 100×) of IMQ-induced mouse inflammatory skin lesion and normal control mice.
Figure 1B:
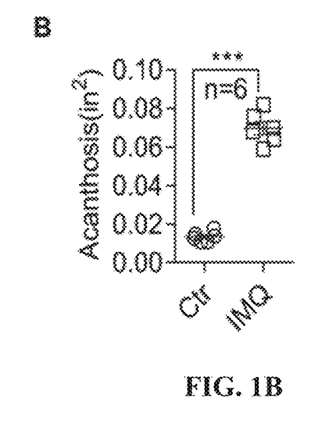
FIG. 1B shows a quantitative result of acanthosis of an IMQ-induced mouse inflammatory skin lesion.
Figure 1C:
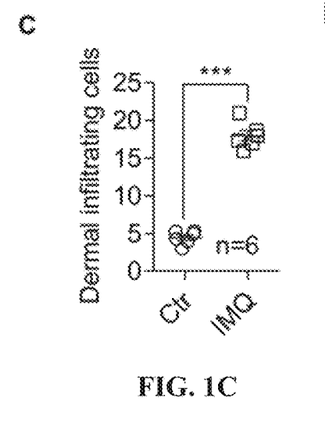
FIG. 1C shows a quantitative result of inflammatory cell infiltration of an IMQ-induced mouse inflammatory skin lesion.

Embodiment 1: Increased Expression of microRNA-210 in IMQ-Induced Mouse Inflammatory Skin Lesion Twelve 7-week-old healthy female Balb/c mice were selected. After the backs are unhaired by 2×2 cm², the mice were randomly divided into two groups: the first group was a Model group, and the unhaired back area of each mouse was externally coated with 5% imiquimod ointment every day for 6 successive days, 62.5 mg/d; and the second group was a Normal group, and the unhaired back area of each mouse was externally coated with matrix ointment every day for 6 successive days, 62.5 mg/d. At the $7^{th}$ day of modeling, the mice in each group were killed by a neck breaking method. Their back skin lesions were taken and put into a formalin solution to be fixed overnight. Dehydration and paraffin embedding were performed. Sections were subjected to HE staining. Histopathological changes were observed under a microscope. The results showed that compared with mice of Normal group, mice of Model group showed macroscopic erythema and scales on the skin, obviously thickened epidermis, hyperkeratosis, parakeratosis, extended rete ridges, acanthosis, disappeared stratum granulosum, dermal inflammatory cell infiltration and obvious angiectasis (FIGS. 1A-1C). It proved that the modeling of IMQ-induced mouse inflammatory skin diseases was successful.

Figure 1D:
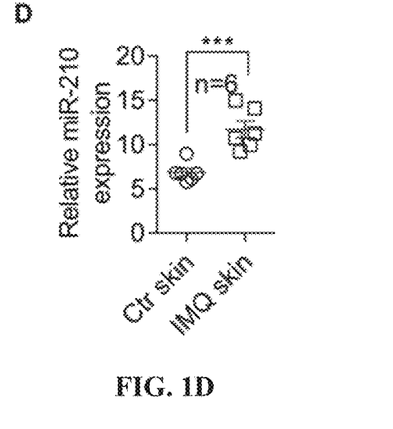
FIG. 1D shows an expression level of miR-210 in IMQ-induced mouse inflammatory skin lesion and normal mouse skin.
Figure 1E:
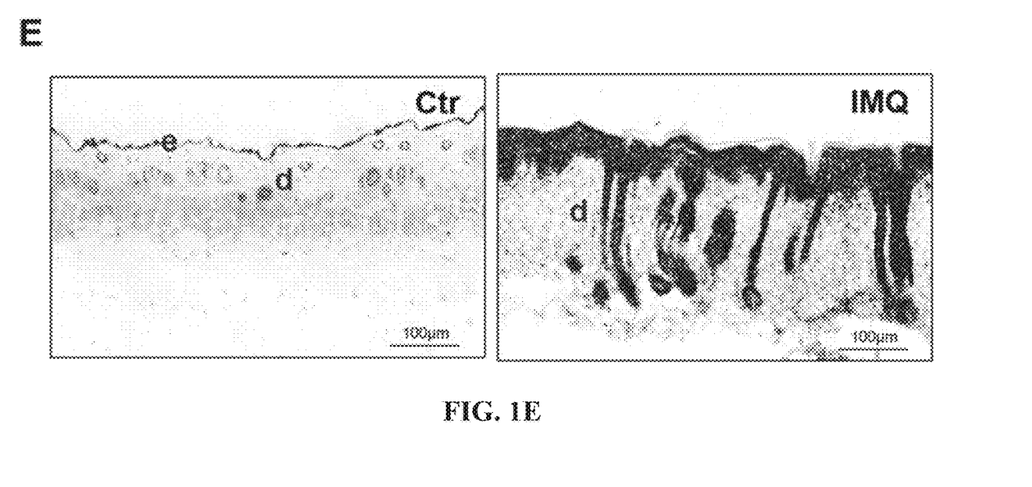
FIG. 1E shows miR-210 in situ hybridization in IMQ-induced mouse inflammatory skin lesion and normal mouse skin.

IMQ-induced mouse inflammatory skin lesion and normal mouse skin tissues were taken. Tissue total RNA was extracted by a Trizol method. After reverse transcription, expression of microRNA-210 was detected through real-time Polymerase Chain Reaction (PCR). At the same time, expression and distribution of microRNA-210 in the IMQ-induced mouse inflammatory skin lesion were detected by an in situ hybridization technology. The results showed that compared with normal skin, the expression of microRNA-210 was significantly up-regulated in IMQ-induced mouse inflammatory skin (FIG. 1D). The in situ hybridization results also showed that the expression of microRNA-210 in the IMQ-induced mouse epidermis was obviously enhanced (FIG. 1E).

FIG. 1A shows IMQ-induced mouse inflammatory skin lesions. FIG. 1B shows epidermis thickness conditions in skin lesions of IMQ mice (n=6) and normal mice (n=6), *P<0.001. FIG. 1C shows inflammatory cell infiltration conditions in skin lesions of IMQ mice (n=6) and normal mice (n=6), *P<0.001. FIG. 1D shows expression conditions of microRNA-210 in skin lesions of IMQ mice (n=6) and normal mice (n=6), ***P<0.001. FIG. 1E shows expression and distribution of microRNA-210 in IMQ-induced mouse skin lesion tissues and normal mouse skin. Statistical analysis is performed by bilateral t test.

Embodiment 2: Study on Effect and Mechanism of Abnormal microRNA-210 Expression on Keratinocytes and T Cells 1) microRNA-210 promotes proliferation of keratinocytes This experiment adopted human primary keratinocytes. The human primary keratinocytes were inoculated into a 96-well plate 12 h (hours, hrs) before transfection, and were cultured for 12 h in a 5% $CO_2$ incubator at 37° C. by a corresponding 100 µL serum-free culture medium. When the cells grew to reach a 90% fusion degree, agomiR-210 (a microRNA-210 mimic), antagomiR-210 and a corresponding negative control were transfected into the keratinocytes. After 6 hrs, a fresh culture medium was used for continuous culture for 24 hrs or 48 hrs. 10 µL of CCK8 solution was added into each well 4 hrs before culture completion. Cell proliferation was detected at wavelength of 450 nm. Results showed that the proliferation of the human primary keratinocytes can be significantly promoted by overexpression of microRNA-210; and oppositely, the proliferation of the keratinocytes can be significantly inhibited by microRNA-210 inhibition (FIGS. 2A-2C).

Figure 2A:
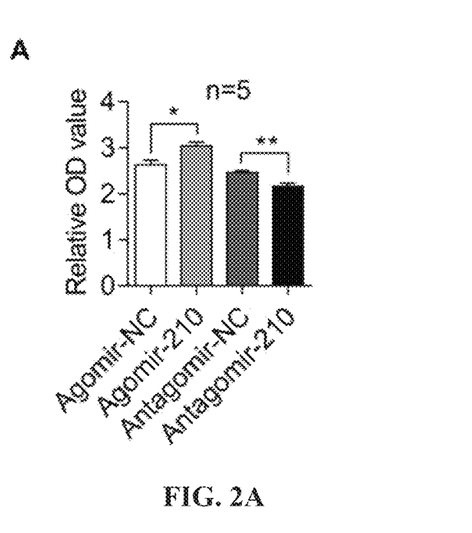
FIG. 2A shows influence of microRNA-210 overexpression or inhibition on proliferation of keratinocytes at 24 h.
Figure 2B:
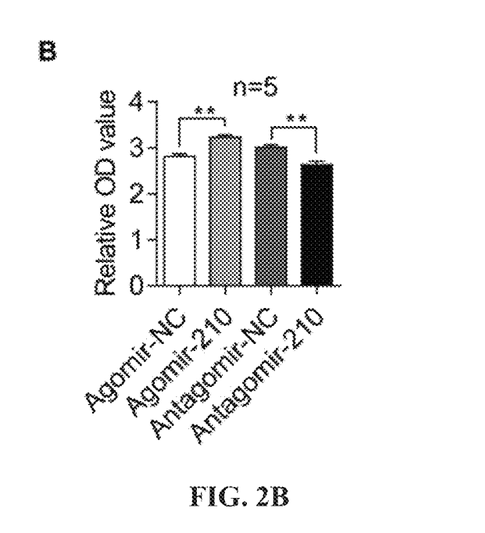
FIG. 2B shows influence of microRNA-210 overexpression or inhibition on proliferation of keratinocytes at 48 h.
Figure 2C:
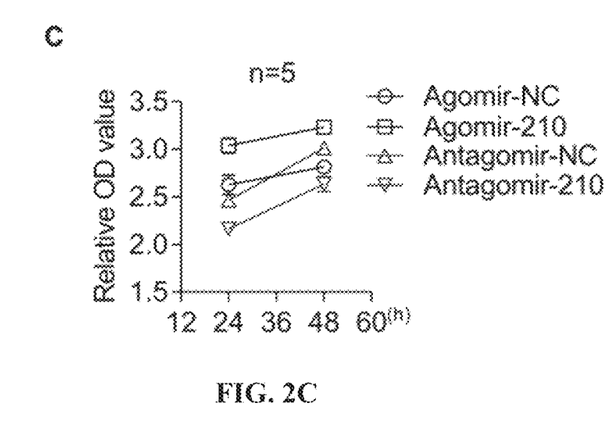
FIG. 2C shows variation trend of keratinocytes proliferation regulated by microRNA-210.

FIG. 2A shows influence of microRNA-210 on proliferation of keratinocytes at 24 h, *P<0.05, and P<0.01. FIG. 2B shows influence of microRNA-210 on proliferation of keratinocytes at 48 h, P<0.01 FIG. 2C shows variation trend of keratinocytes proliferation regulated by microRNA-210. Statistical analysis is performed by bilateral t test.

2) microRNA-210 promotes keratinocytes to secret a chemokine CCL20, which further influences T cell migration This experiment adopted human primary keratinocytes. The human primary keratinocytes were inoculated into a 24-well plate containing 1 ml of serum-free culture medium 12 hrs before transfection for culture for 12 h in a 5% $CO_2$ incubator at 37° C. When the cells grew to reach a 90% fusion degree, agomiR-210 (a microRNA-210 mimic), antagomiR-210 and a corresponding negative control were transfected into the keratinocytes. After 6 hrs, fresh culture medium was used for continuous culture for 48 hrs. Cells were collected. Total RNA was extracted, and expression levels of cytokines and chemokines were detected through real-time PCR. The results showed that the chemokine CCL20 secretion of keratinocytes can be significantly promoted by overexpression of microRNA-210 (FIG. 3A), and was obviously inhibited by microRNA-210 inhibition (FIG. 3B).

The cells were cultured by the same method and cell supernatant was collected. One part was used for ELISA detection of protein secretion level of CCL20. The result was consistent with the above PCR result (FIG. 3C). The other part was used for a subsequent chemotaxis experiment. Small chemotaxis chambers with a 5.0 µm pore diameter were used for the chemotaxis experiment. CD4+ T cells were separated from normal human peripheral blood using magnetic beads. $5 \times 10^5$ CD4+ T cells were resuspended by 200 µL serum-free culture medium and were inoculated in an upper chamber. 600 μL of keratinocyte cultural supernatant was inoculated in a lower chamber. Culture was performed for 90 min in a 5% $CO_2$ incubator at 37° C. Non-chemotactic cells of the upper chamber were slightly scraped away by cotton swabs. Chemotactic cells on the lower layer surface of filter screen were fixed by 90% alcohol for 15 min. Then, staining was performed for 10 min by 0.1% crystal violet. Phosphate buffer saline (PBS) rinsing was performed twice. The numbers of chemotactic cells in five different view fields were counted under a microscope, and a mean value was taken. The results showed that the supernatant secreted by keratinocytes overexpressing microRNA-210 can significantly promote T cell migration, and the supernatant secreted by keratinocytes with microRNA-210 inhibition can significantly inhibit the T cell migration FIGS. 3D and 3E.

Figure 3A:
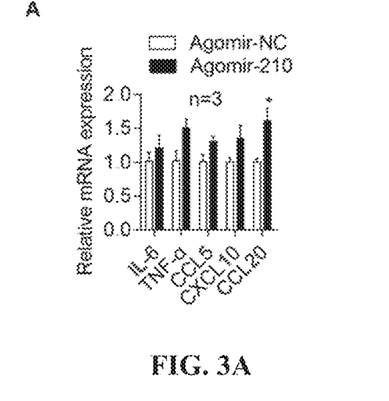
FIG. 3A shows influence of microRNA-210 overexpression on chemokine and inflammatory factor secretion of keratinocytes.
Figure 3B:
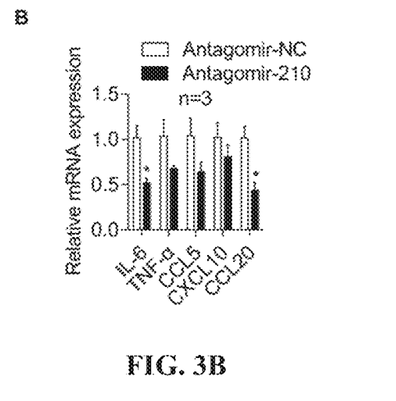
FIG. 3B shows influence of microRNA-210 inhibition on chemokine and inflammatory factor secretion of keratinocytes.
Figure 3C:
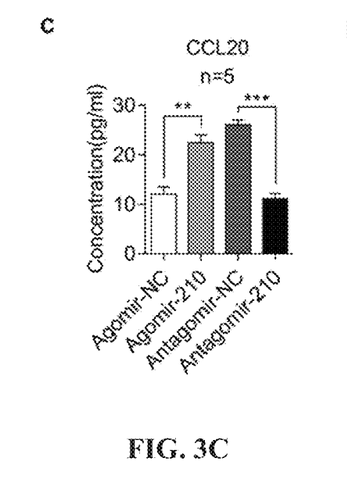
FIG. 3C shows influence of microRNA-210 overexpression or inhibition on CCL20 secretion in keratinocyte cultural supernatant.
Figure 3D:
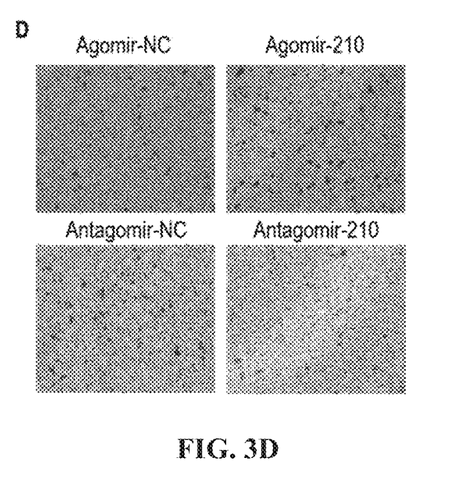
FIG. 3D shows representative view fields of chemotactic cells under the microscope.
Figure 3E:
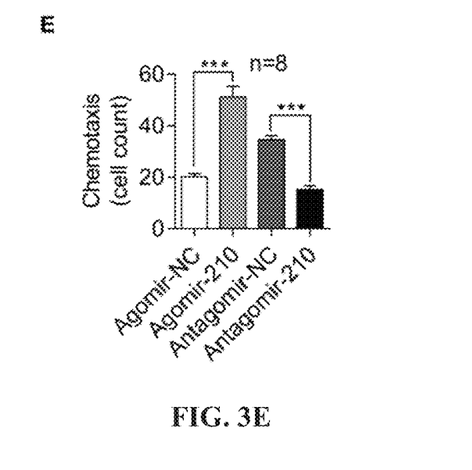
FIG. 3E shows the mean values of chemotactic cell numbers counted from the view fields.

FIG. 3A shows influence of microRNA-210 overexpression on chemokine and cytokine secretion of keratinocytes, *P<0.05. FIG. 3B shows influence of microRNA-210 inhibition on chemokine and inflammatory factor secretion of keratinocytes. *P<0.05. FIG. 3C shows influence of microRNA-210 overexpression or inhibition on chemokine CCL20 protein secretion of keratinocytes, P<0.01, *P<0.001. FIGS. 3D and 3E show influence of microRNA-210 overexpression or inhibition on T cell chemotaxis capability of keratinocytes, ***P<0.001. Statistical analysis is performed by bilateral t test.

3) microRNA-210 promotes cell differentiation of $T_H1$ and $T_H17$ and inhibits cell differentiation of $T_H2$ Normal human peripheral blood was collected and naïve $CD4^+$ T cells was separated by magnetic beads. Firstly, expression change of miR-210 during the differentiation of naïve $CD4^+$ T cells to different T cell subsets was detected. Then, agomiR-210, antagomiR-210 and corresponding control were respectively transfected into the naïve $CD4^+$ T cells. Under in vitro differentiation induction conditions, the naïve $CD4^+$ T cells were induced to differentiate to $T_H1$, $T_H2$, $T_H17$ and $iT_{reg}$. After 5 days, differentiation percentage of different T cell subsets in each experiment group was detected by flow cytometry. The result showed that the expression of microRNA-210 was most significantly increased during $T_H17$ cell in vitro differentiation (FIG. 4A); differentiation of the naïve $CD4^+$ T cells to $T_H1$ and $T_H17$ can be significantly promoted, and the differentiation of $T_H2$ was inhibited by overexpression of microRNA-210 (FIG. 4B); differentiation of the naïve $CD4^+$ T cells to $T_H1$ and $T_H17$ can be inhibited, and the differentiation of $T_H2$ was promoted by microRNA-210 inhibition (FIG. 4C): and the microRNA-210 had no significant influence on in vitro Treg differentiation induction (FIGS. 4B and 4C).

Figure 4A:
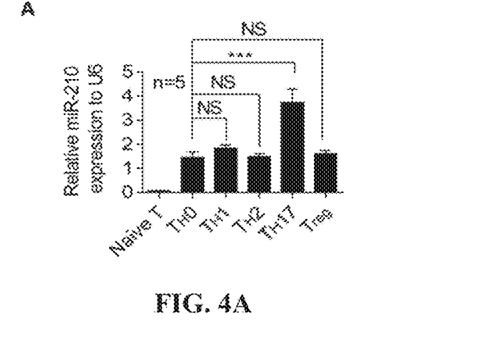
FIG. 4A shows expression change of microRNA-210 during the differentiation of naïve CD4$^+$ T cells to different T cell subsets.
Figure 4B:
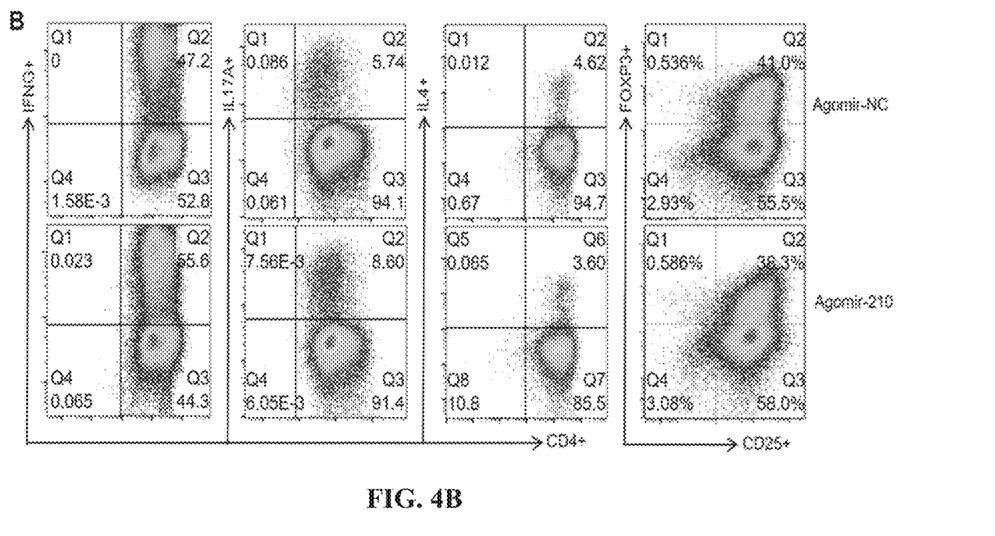
FIG. 4B shows influence of microRNA-210 overexpression on differentiation of different T cell subsets.
Figure 4C:
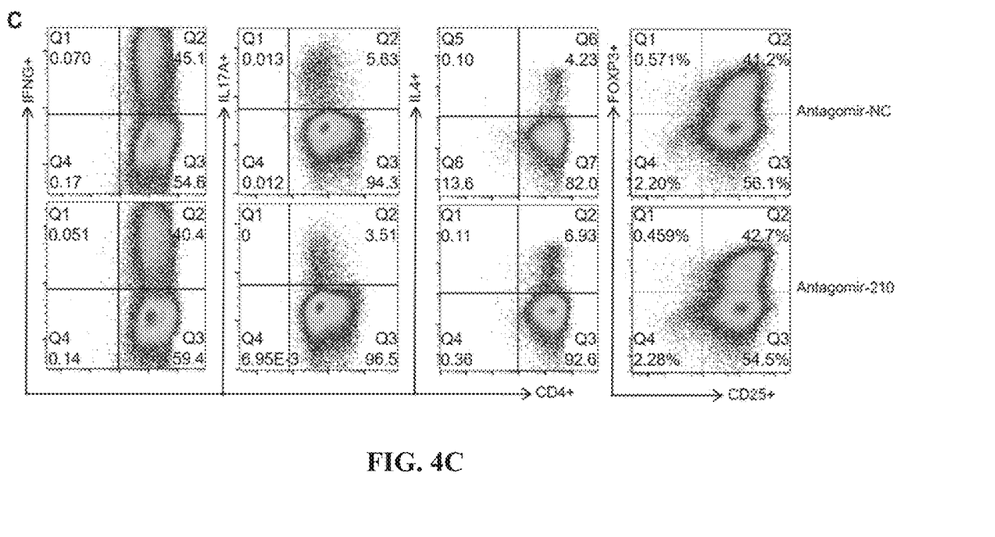
FIG. 4C shows influence of microRNA-210 inhibition on differentiation of different T cell subsets.

FIG. 4A shows expression change of microRNA-210 during the differentiation of naïve $CD4^+$ T cells to different T cell subsets, ***P<0.001. NS represents no statistical significance. Statistical analysis is performed by one-way analysis of variance. FIG. 4B shows influence of microRNA-210 overexpression on differentiation of different T cell subsets FIG. 4C shows influence of microRNA-210 inhibition on differentiation of different T cell subsets.

4) microRNA-210 promotes secretion of IL-17A, IL-17F and IFN-γ and inhibits secretion of IL-4 in $CD4^+$ T cells We transfected agomiR-210, antagomiR-210 and their corresponding negative control to normal human peripheral blood $CD4^+$ T cells. After 48 h, cell supernatant and cells were collected. The transfection efficiency and the protein and mRNA level change of cytokines were respectively detected by ELISA and real-time PCR methods. The results showed that agomiR-210 or antagomiR-210 can significantly promote or inhibit the expression of microRNA-210 in the $CD4^+$ T cells (FIG. 5A); the secretion of IL-17A, IL-17F and IFN-γ can be significantly promoted, and the secretion of IL-4 was inhibited by overexpression of microRNA-210 (FIGS. 5B and 5D); and the secretion of IL-17A. IL-17F and IFN-γ can be significantly inhibited, and the secretion of IL-4 was promoted by microRNA-210 inhibition (FIGS. 5C and 5E).

Figure 5A:
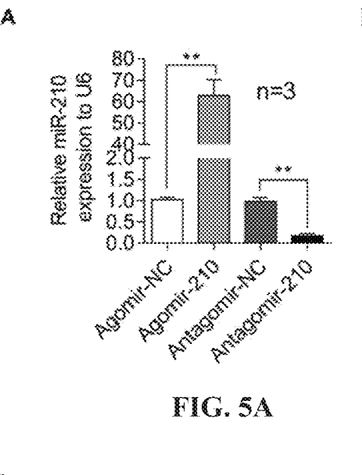
FIG. 5A shows that agomiR-210 or antagomiR-210 can significantly promote or inhibit expression of microRNA-210 in CD4$^+$ T cells.
Figure 5B:
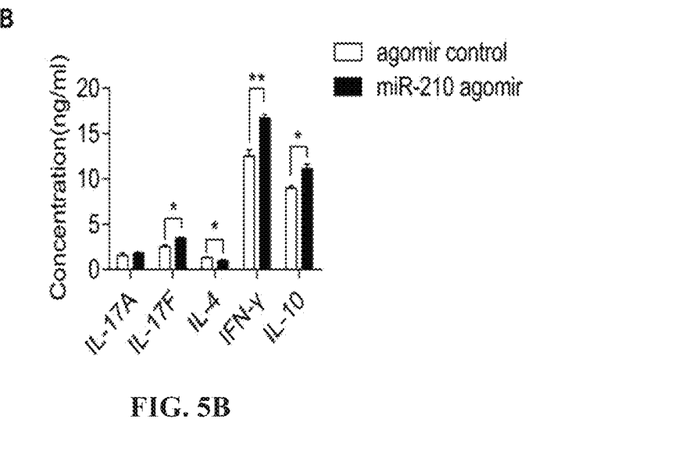
FIG. 5B shows influence of overexpression of microRNA-210 on cytokine protein level in CD4$^+$ T cell cultural supernatant.
Figure 5C:
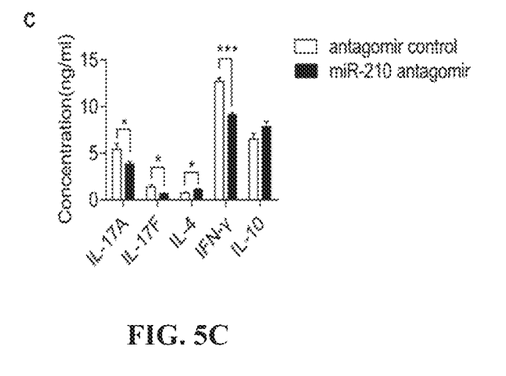
FIG. 5C shows influence of inhibition of microRNA-210 on cytokine protein level in CD4$^+$ T cell cultural supernatant.
Figure 5D:
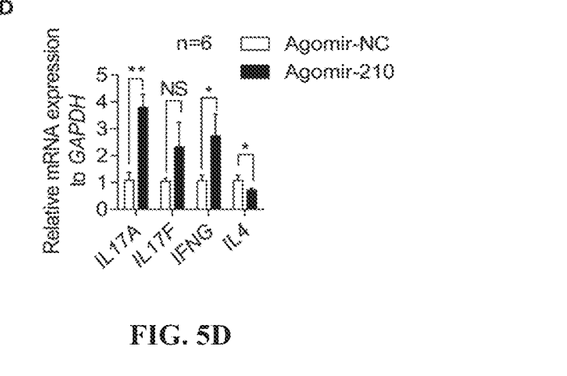
FIG. 5D shows influence of overexpression of microRNA-210 on cytokine mRNA level in CD4$^+$ T cells.
Figure 5E:
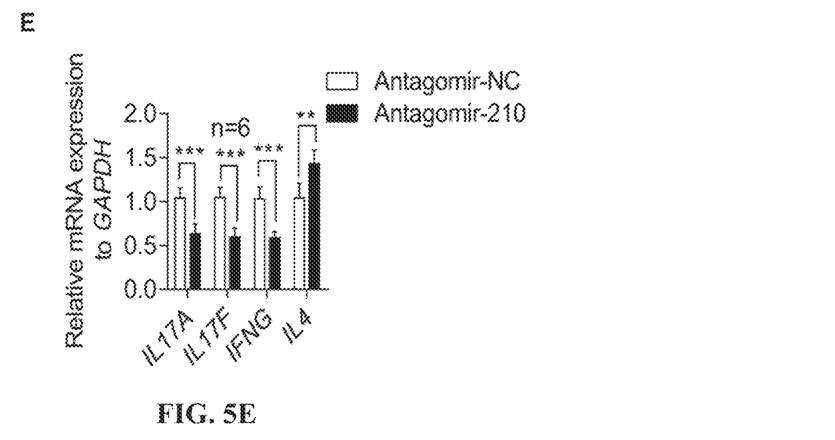
FIG. 5E shows influence of inhibition of microRNA-210 on cytokine mRNA level in CD4$^+$ T cells.

FIG. 5A shows that agomiR-210 or antagomiR-210 can significantly promote or inhibit expression of microRNA-210 in $CD4^+$ T cells, **P<0.01. FIGS. 5B and 5C show the influence of overexpression or inhibition of microRNA-210 on cytokine protein level in $CD4^+$ T cell cultural supernatant, *P<0.05, P<0.01, *P<0.001. FIGS. 5D and 5E show the influence of overexpression or inhibition of microRNA-210 on cytokine mRNA level in $CD4^+$ T cells, *P<0.05, P<0.01, *P<0.001. NS represents no statistical significance. Statistical analysis is performed by bilateral t test.

Figure 6A:
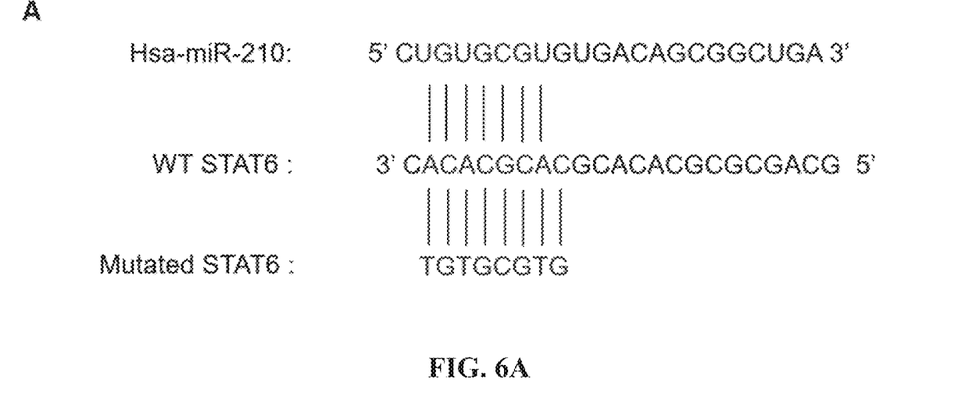
FIG. 6A shows a binding site sequence of an mRNA 3' non-coding area of a target gene STAT6 with microRNA-210 and a binding site sequence after mutation.
Figure 6B:
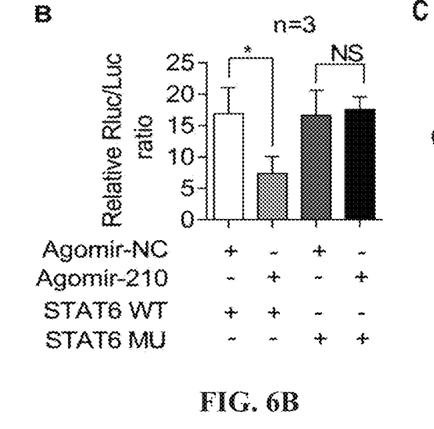
FIG. 6B shows results of the luciferase reporter gene experiment.
Figure 6C:
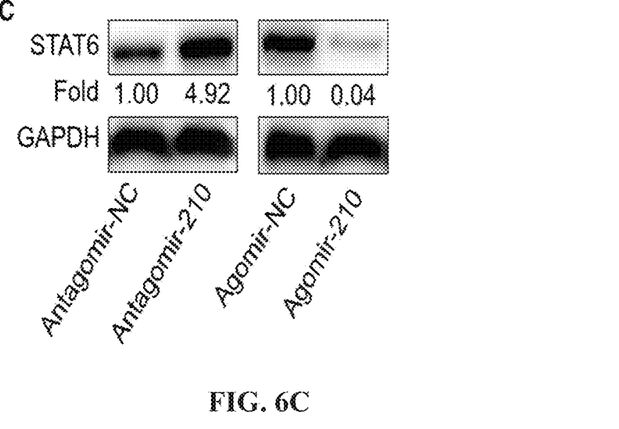
FIG. 6C shows immunoblots for the expression level of STAT6 protein
Figure 6D:
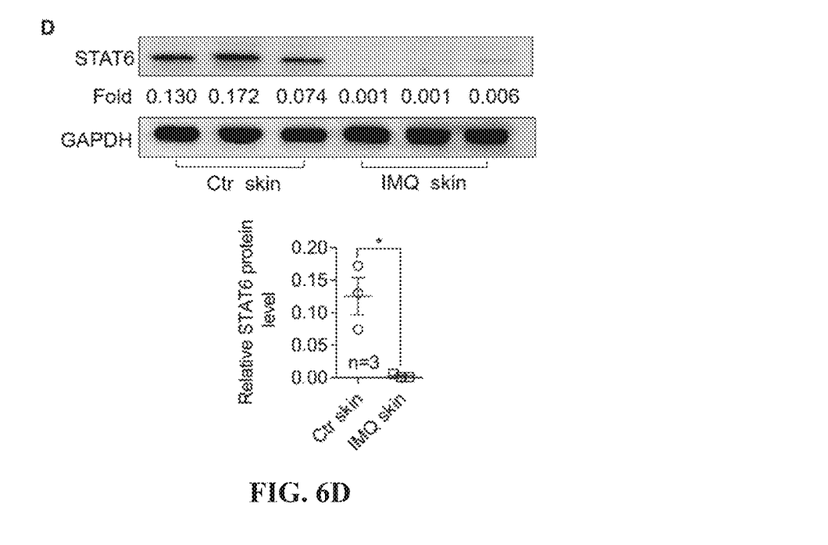
FIG. 6D shows the expression level of STAT6 protein in IMQ-induced mouse skin lesion tissues (n=3) and normal mouse skin tissues (n=3).

5) downstream target gene screening and verification of microRNA-210 Firstly, through bioinformatics software such as TargetScan, miRWalk, miRanda and RNA22, we predicted and discovered that STAT6 may be a downstream target gene of microRNA-210, and may be closely related to differentiation of T cells (FIG. 6A). Secondly, we further performed luciferase reporter gene experimental verification in HEK293T cells, and discovered that luciferase activity in the HEK293T cells transfected with wild type plasmids (STAT6 WT) can be significantly inhibited by overexpression of microRNA-210, however, luciferase activity in the HEK293T cells transfected with STAT6 binding site mutation plasmids (STAT6 MU) was not influenced (FIG. 6B). Then, we performed microRNA-210 overexpression and interference experiments in human $CD4^+$ T cells, and proved that microRNA-210 can regulate the protein expression level of STAT6 (FIG. 6C). Additionally, we also detected the protein level of the target gene STAT6 in an IMQ-induced mouse model skin lesion by western blot, and discovered that compared with normal mouse skin, the IMQ-induced mouse skin had significantly down-regulated expression level of STAT6 protein in the skin lesion thereof (FIG. 6D).

FIG. 6A shows a binding site sequence of an mRNA Y non-coding area of a target gene STAT6 with microRNA-210 and a binding site sequence after mutation (red area). FIG. 6B shows an mRNA 3' non-coding area of STAT6 is a direct target of microRNA-210 verified by luciferase reporter gene experiment, *P<0.05. FIG. 6C shows that microRNA-210 can regulate the expression level of STAT6 protein. FIG. 6D shows the expression level of STAT6 protein in IMQ-induced mouse skin lesion tissues (n=3) and normal mouse skin tissues (n=3), *P<0.05. Statistical analysis is performed by bilateral t test.

The present embodiment proves that microRNA-210 can directly regulate the expression of its target gene STAT6. The proliferation and the chemokine CCL20 secretion of the keratinocytes can be significantly inhibited by microRNA-210 inhibition. The chemotactic inflammatory T cell migration towards skin lesion is further prevented. At the same time, the differentiation of $T_H1$ and $T_H17$ cells can be significantly inhibited, and the differentiation of $T_H2$ cells is promoted by microRNA-210 inhibition.

Figure 7A:
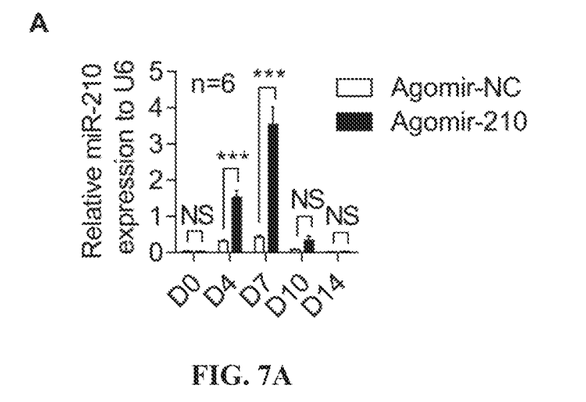
FIG. 7A shows expression change of microRNA-210 in an injection process of agomiR-210.

Embodiment 3: In Vivo Overexpression of microRNA-210 can Significantly Promote and Aggravate IMQ-Induced Mouse Inflammatory Skin Lesion 6- to 8-week-old healthy female Balb/c mice were selected. The backs are unhaired by 2×2 $cm^2$. The mice were randomly divided into two groups: 1) agomiR-210 group: the back of each mouse in this group was externally coated with 5% IMQ ointment every day for 6 successive days, 62.5 mg/d, and intradermal injection of 150 μl (5 nmol) of agomiR-210 was performed on the back at $0^{th}$ day, $1^{st}$ day, $2^{nd}$ day and $3^{rd}$ day: and 2) agomiR-NC group: the back of each mouse in this group was externally coated with 5% IMQ ointment every day for 6 successive days, 62.5 mg/d, and intradermal injection of 150 μl (5 nmol) of agomiR-NC was performed on the back at $0^{th}$ day, $1^{st}$ day, $2^{nd}$ day and $3^{rd}$ day. Three mice in each group were killed respectively at $4^{th}$ day, $7^{th}$ day, $10^{th}$ day and $14^{th}$ day of modeling. Clinic and pathological changes of the skin lesions were observed, and histological analysis was performed. Expression change of microRNA-210 was detected through real-time PCR. The results showed that at $4^{th}$ day and $7^{th}$ day of modeling, the expression of microRNA-210 was significantly increased in the agomiR-210 group (FIG. 7A). Through intradermal injection of agomiR-210, the IMQ-induced mouse inflammatory skin lesion can be significantly promoted and aggravated. Splenomegaly of mice in the agomiR-210 group was obviously aggravated than that of the mice in the agomiR-NC group. The above indexes reached the peak at 7 day, exhibiting the most significant difference. In a disease recovery period ($8^{th}$ to $14^{th}$ days), the clinic and pathological changes of the two groups had no significant differences (FIGS. 7B-7F).

Figure 7B:
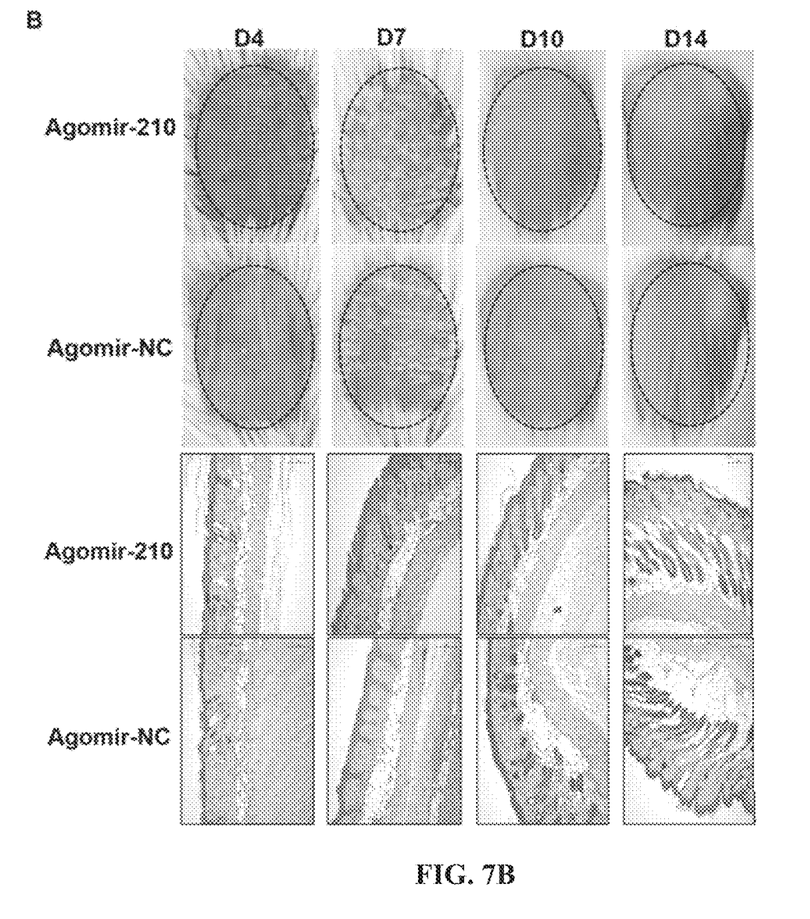
FIG. 7B shows appearance and HE staining pathological change of mice in agomiR-210 group and agomiR-NC group at the fourth, seventh, tenth and fourteenth day.
Figure 7C:
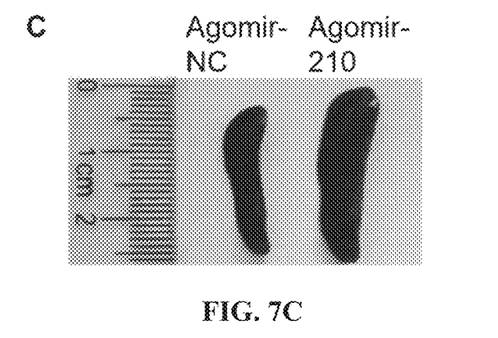
FIG. 7C shows splenomegaly conditions of mice in agomiR-210 group and agomiR-NC group at the seventh day.
Figure 7D:
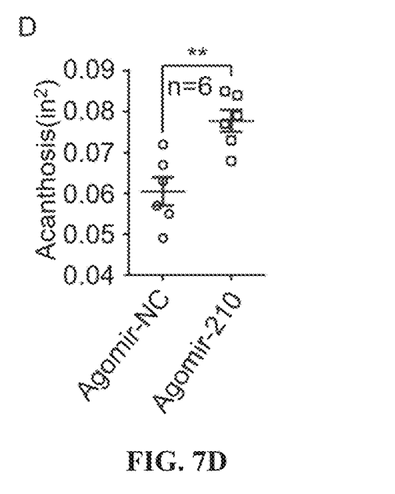
FIG. 7D shows epidermis thickening conditions in skin lesions of mice in agomiR-210 group (n=6) and agomiR-NC group (n=6) at the seventh day, **P<0.01.
Figure 7E:
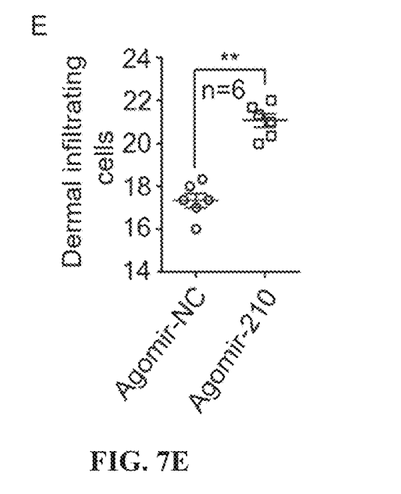
FIG. 7E shows inflammatory cell infiltration conditions in skin lesions of mice in agomiR-210 group (n=6) and agomiR-NC group (n=6) at the seventh day.
Figure 7F:
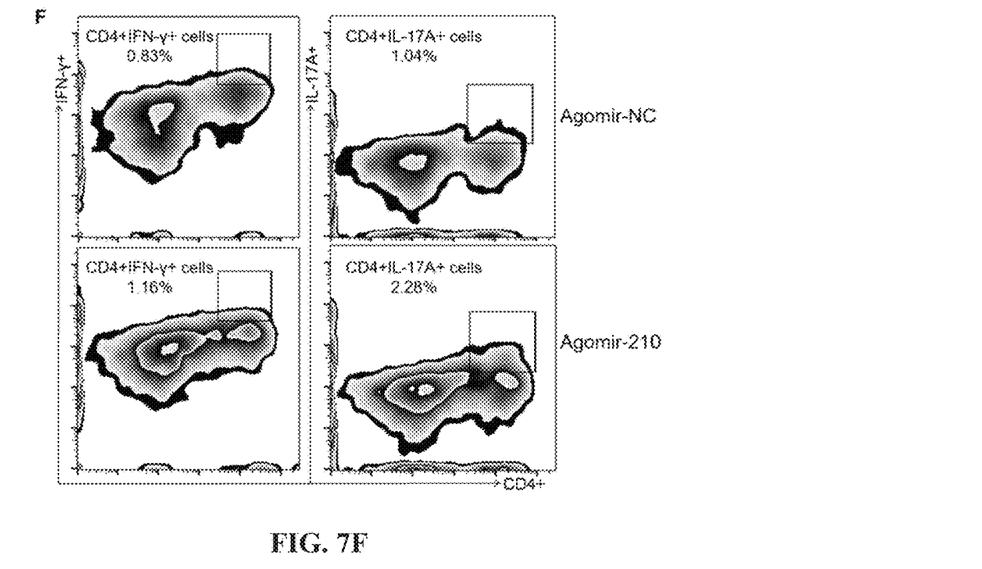
FIG. 7F shows proportion change of $T_H1$ and $T_H17$ cells in a dermal single-cell suspension of skin lesions of mice in agomiR-210 group and agomiR-NC group at the seventh day.

FIG. 7A shows expression change of microRNA-210 in an injection process of agomiR-210, *P<0.001. FIG. 7B shows appearance and HE staining pathological change of mice in agomiR-210 group and agomiR-NC group at the fourth, seventh, tenth and fourteenth day FIG. 7C shows splenomegaly conditions of mice in agomiR-210 group and agomiR-NC group at the seventh day. FIG. 7D shows epidermis thickening conditions in skin lesions of mice in agomiR-210 group (n=6) and agomiR-NC group (n=6) at the seventh day, P<0.01. FIG. 7E shows inflammatory cell infiltration conditions in skin lesions of mice in agomiR-210 group (n=6) and agomiR-NC group (n=6) at the seventh day, **P<0.01. FIG. 7F shows proportion change of $T_H1$ and $T_H17$ cells in a dermal single-cell suspension of skin lesions of mice in agomiR-210 group and agomiR-NC group at the seventh day. Statistical analysis is performed by bilateral t test.

Experiment 4: Specific microRNA-210 Knockout can Alleviate IMQ-Induced Mouse Inflammatory Skin Lesion C57BL/6J background microRNA-210 knockout mice (miR-210 KO mice) were constructed. 6-8-week-old KO mice and WT mice were selected. The unhaired back area was externally coated with 5% IMQ ointment every day for 6 successive days, 62.5 mg/d. At $7^{th}$ day, the mice in each group were killed. Histopathological analysis and splenic T cell subset proportion detection were performed. The results showed that the IMQ-induced mouse inflammatory skin lesion can be significantly inhibited, and the splenic T cell immunologic derangement was mitigated in KO mice (FIG. 8).

Figure 8A:
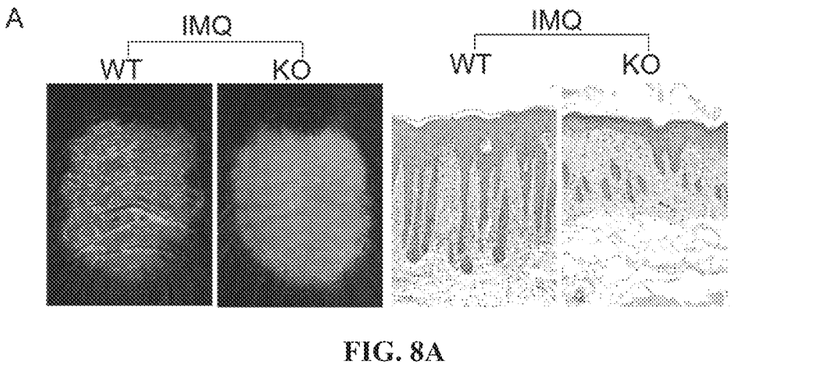
FIG. 8A shows photographs of IMQ-induced mouse inflammatory skin lesion in KO mice and WT mice.
Figure 8B:
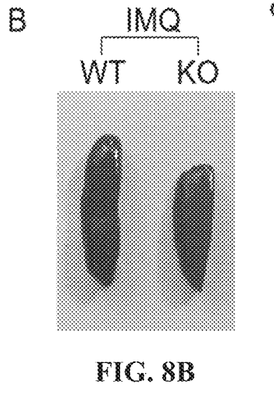
FIG. 8B shows splenomegaly conditions of IMQ-induced KO mice and WT mice
Figure 8C:
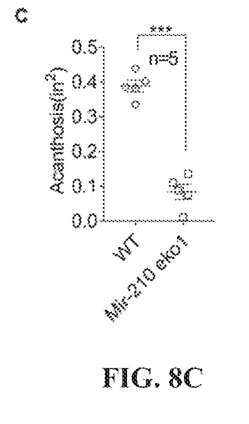
FIG. 8C shows epidermis thickening conditions in skin lesions of IMQ-induced KO mice (n=5) and WT mice (n=5).
Figure 8D:
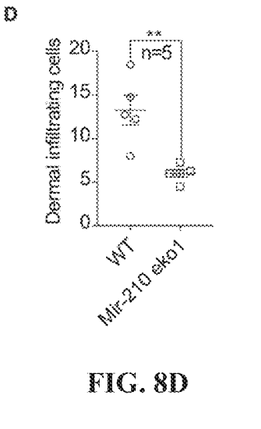
FIG. 8D shows inflammatory cell infiltration conditions in skin lesions of IMQ-induced KO mice (n=5) and WT mice (n.=5).
Figure 8E:
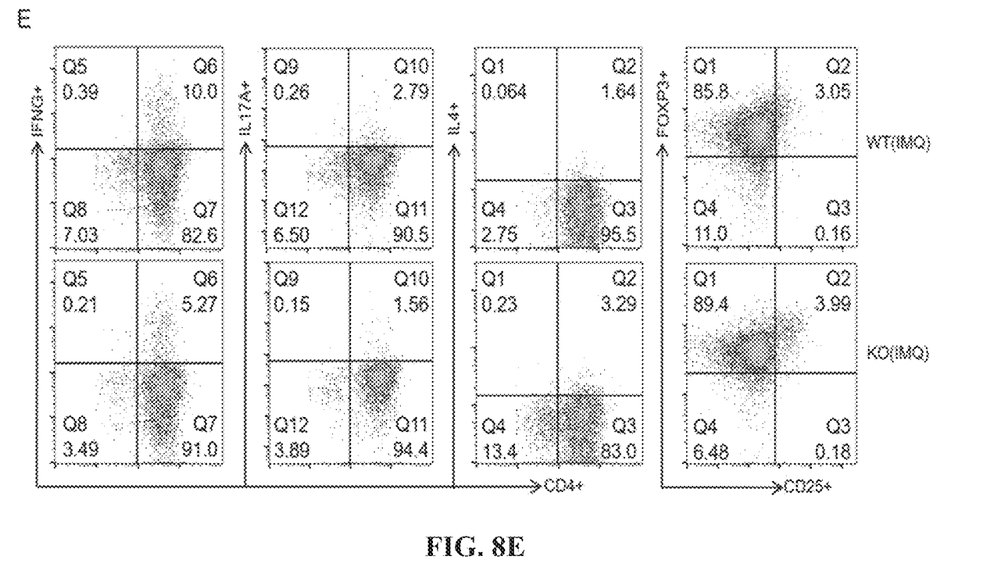
FIG. 8E shows T cell immunologic derangement conditions in spleens of IMQ-induced KO mice and WT mice.

FIG. 8A shows appearance change and HE pathological images of inflammatory skin lesions of IMQ-induced miR-210 KO mice and WT mice. FIG. 8B shows splenomegaly conditions of IMQ-induced KO mice and WT mice. FIG. 8C shows epidermis thickening conditions in skin lesions of IMQ-induced KO mice (n=5) and WT mice (n=5), *P<0.001. FIG. 8D shows inflammatory cell infiltration conditions in skin lesions of IMQ-induced KO mice (n=5) and WT mice (n=5), P<0.01. FIG. 8E shows T cell immunologic derangement conditions in spleens of IMQ-induced KO mice and WT mice. Through microRNA-210 knockout, the $T_H1$ and $T_H17$ proportion in the IMQ-induced mouse splenic cells can be significantly reduced, and the $T_H2$ cell proportion is increased. Statistical analysis is performed by bilateral t test.

Embodiment 5: Intradermal Injection of a microRNA-210 Inhibitor on a Skin Lesion can Significantly Mitigate the Mouse Inflammatory Skin Lesion Twelve 6-week-old healthy female Balb/c mice were selected. Three-point intradermal injection was performed on back unhaired areas by using cholesterol-modified antagomiR-210 (cholesterol was connected to a 5' end of antagomiR-210 to enhance its transmembrane property, and expression of microRNA-210 can be specifically inhibited). The mice were divided into two groups in experiments: (1) antagomiR-210 group: the back was externally coated with 5% IMQ ointment every day for 6 successive days. 62.5 mg/d, and intradermal injection of 150 μl of antagomiR-210 was performed on the back at $0^{th}$ day, $1^{st}$ day, $2^{nd}$ day and $3^{rd}$ day, and 2) antagomiR-NC group: the back was externally coated with 5% IMQ ointment every day for 6 successive days, 62.5 mg/d, and intradermal injection of 150 μl of antagomiR-NC was performed on the back at $0^{th}$ day, $1^{st}$ day, $2^{nd}$ day and $3^{rd}$ day. The back skin lesions were taken after 1 week. One part was fixed overnight by a formalin solution, dehydration and paraffin embedding. Sections were subjected to HE staining. Histopathological changes were observed. The other part was subjected to tissue RNA extraction, and the expression of microRNA-210 was detected through real-time PCR. The results showed that through injection of the cholesterol-modified antagomiR-210, the expression of microRNA-210 in the skin lesions can be significantly inhibited, and the mouse inflammatory skin lesion was obviously mitigated (FIGS. 9A and 9B); and histopathologically, antagomir-210 can significantly inhibit epidermis thickening, rete ridges extension and dermal inflammatory cell infiltration (FIGS. 9C-9E), and significantly mitigated pathological changes of the IMQ-induced mouse inflammatory skin lesions. At the same time, through intradermal injection of the antagomiR-210, the T cell immunologic derangement in the spleens of the IMQ-induced mice can be significantly mitigated (FIG. 10).

Figure 9A:
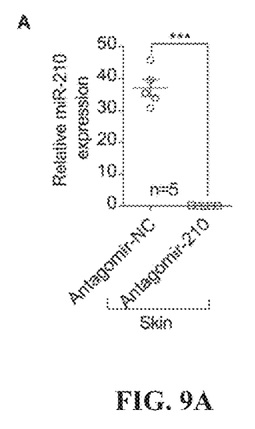
FIG. 9A shows levels of expression of microRNA-210 in the skin lesions.
Figure 9B:
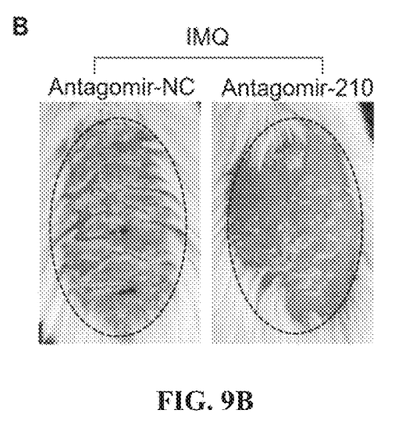
FIG. 9B shows photographs of IMQ-induced mouse inflammatory skin lesion.
Figure 9C:
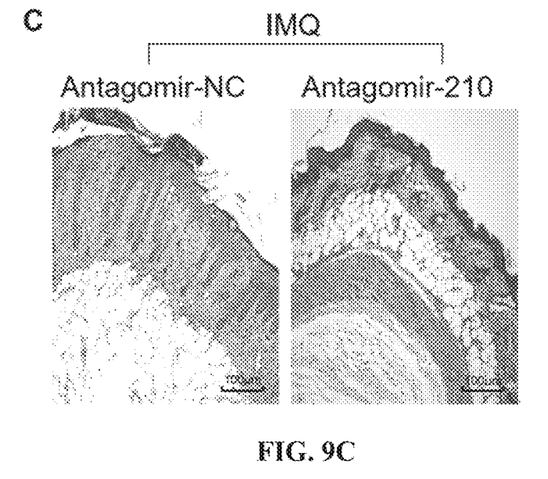
FIG. 9C shows skin sections.
Figure 9D:
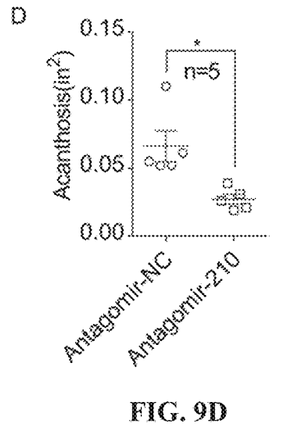
FIG. 9D shows levels of acanthosis in the skin lesions.
Figure 9E:
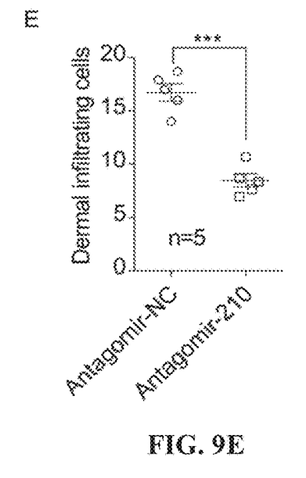
FIG. 9E shows levels of dermal infiltrating cells.
Figure 10:
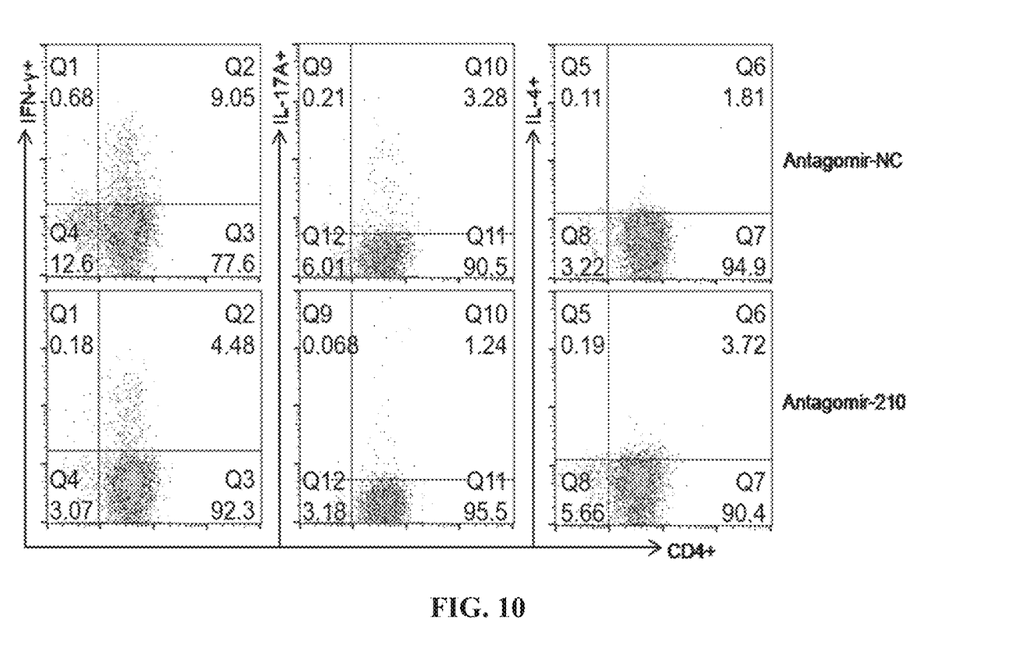
FIG. 10 shows that IMQ-induced mouse T cell immunologic derangement in splenic cells can be significantly mitigated through intradermal injection of antagomiR-210 on a skin lesion.

FIG. 9A shows expression conditions of microRNA-210 in skin lesions of mice in antagomiR-210 group (n=5) and antagomiR-NC group (n=5), ***P<0.001. FIG. 9B shows appearance performance of mouse inflammatory skin lesions in antagomiR-210 group and antagomiR-NC group. FIG. 9C shows pathological changes of inflammatory skin lesions of mice in antagomiR-210 group and antagomiR-NC group FIG. 9D shows epidermis thickening conditions in skin lesions of mice in antagomiR-210 group (n=5) and antagomiR-NC group (n1=5), *P<0.05. FIG. 9E shows inflammatory cell infiltration conditions in skin lesions of mice in antagomiR-210 group (n=5) and antagomiR-NC group (n=5), ***P<0.001. FIG. 10 shows T cell immunologic derangement conditions in spleens of mice in antagomiR-210 group and antagomiR-NC group. Through intradermal injection of microRNA-210, the $T_H1$ and $T_H17$ proportion in the IMQ-induced mouse spleen cells can be significantly reduced, and the $T_H2$ cell proportion is increased. Statistical analysis is performed by bilateral t test.

The foregoing are merely exemplary embodiments of the present invention, and are illustrative and not restrictive for the present invention. It is to be understood by those of ordinary skill in the art that, many changes, modifications, or even equivalent changes may be made to the present invention within the principle and scope limited in the claims of the present invention, but all of them fall within the protection scope of the present invention.

What is claimed is:

1. A method comprising the step preparing a drug for treating inflammatory skin diseases including by providing a pharmaceutically effective amount of a modified microRNA-210 inhibitor, wherein the modified microRNA-210 inhibitor inhibits the expression of microRNA-210 as set forth in SEQ ID NO: 1, wherein the modified microRNA-210 inhibitor comprises a sequence set forth in SEQ ID NO: 2 which has been modified to include 3'-cholesterol and 5'-OMe, and the microRNA-210 inhibitor after modification retains inhibiting activity of the microRNA-210 inhibitor of SEQ ID NO: 2 against the expression of microRNA-210 having SEQ ID NO: 1.

2. The method according to claim 1, wherein the inflammatory skin diseases comprise psoriasis, atopic dermatitis, eczema or parapsoriasis.

3. The method according to claim 1, wherein the drug for treating inflammatory skin disease including a modified microRNA-210 inhibitor is prepared for administration by injection to skin lesions.

4. A method comprising the step of administering a modified microRNA-210 inhibitor to a subject, wherein the modified microRNA-210 inhibitor is used for inhibiting secretion of IL-17A, IL-17F and IFN-γ and promoting secretion of IL-4, and a sequence encoding microRNA-210 is set forth in SEQ ID NO: 1, wherein the modified microRNA-210 inhibitor comprises a sequence set forth in SEQ ID NO: 2 which has been modified to include 3'-cholesterol and 5'-OMe.

5. A method comprising the step of administering a modified microRNA-210 inhibitor to a subject, wherein the modified microRNA-210 inhibitor is used for enhancing expression of a target gene STAT6, and a sequence encoding microRNA-210 is set forth in SEQ ID NO: 1, wherein the modified microRNA-210 inhibitor comprises a sequence set forth in SEQ ID NO: 2 which has been modified to include 3'-cholesterol and 5'-OMe.

6. A method comprising the step of administering a modified microRNA-210 inhibitor to a subject, wherein the modified microRNA-210 inhibitor is used for inhibiting proliferation and chemokine CCL20 secretion of keratinocytes and further inhibiting chemotactic T cell migration towards skin lesions, and a sequence encoding microRNA-210 is set forth in SEQ ID NO: 1, wherein the modified microRNA-210 inhibitor comprises a sequence set forth in SEQ ID NO: 2 which has been modified to include 3'-cholesterol and 5' OMe.

7. A method comprising the step of administering a modified microRNA-210 inhibitor to a subject, wherein the modified microRNA-210 inhibitor is used for inhibiting differentiation of $T_H1$ and $T_H17$ and prompting cell differentiation of $T_H2$, and a sequence encoding microRNA-210 is set forth in SEQ ID NO: 1, wherein the modified microRNA-210 inhibitor comprises a sequence set forth in SEQ ID NO: 2 which has been modified to include 3'-cholesterol and 5'-OMe.

* * * * *